United States Patent
Wigger et al.

[11] Patent Number: 5,672,564
[45] Date of Patent: Sep. 30, 1997

[54] AQUEOUS, MULTIPHASE, STABLE FINISHED FORMULATION FOR CROP PROTECTION ACTIVE COMPOUNDS AND ITS PREPARATION

[75] Inventors: August Wigger, Neuhofen; Hans-Michael Fricke, Limburgerhof; Uwe Kardorff, Mannheim; Adolf Parg, Bad Durkheim; Reiner Kober, Fussgoenheim, all of Germany

[73] Assignee: BASF Aktiengesellschaft, Ludwigshafen, Germany

[21] Appl. No.: 569,124

[22] PCT Filed: Jun. 27, 1994

[86] PCT No.: PCT/EP94/02085

§ 371 Date: Jan. 3, 1996

§ 102(e) Date: Jan. 3, 1996

[87] PCT Pub. No.: WO95/01722

PCT Pub. Date: Jan. 19, 1995

[30] Foreign Application Priority Data

Jul. 3, 1993 [DE] Germany .......................... 43 22 211.0

[51] Int. Cl.$^6$ ...................................................... A01N 25/30
[52] U.S. Cl. .......................... 504/116; 504/234; 504/237; 504/330; 71/DIG. 1; 424/405; 514/376; 514/383; 514/395; 514/941

[58] Field of Search ..................... 504/116, 234, 504/237, 330; 71/DIG. 1; 424/405; 514/376, 383, 395, 941

[56] References Cited

U.S. PATENT DOCUMENTS

| | | | |
|---|---|---|---|
| 4,305,750 | 12/1981 | Kleuser et al. | 71/92 |
| 4,875,929 | 10/1989 | Morgan et al. | 71/121 |
| 5,073,189 | 12/1991 | Bell | 71/92 |
| 5,362,707 | 11/1994 | Fiard et al. | |

*Primary Examiner*—S. Mark Clardy
*Attorney, Agent, or Firm*—Oblon, Spivak, McClelland, Maier & Neustadt, P.C.

[57] ABSTRACT

An aqueous, multiphase, stable finished formulation for crop protection active compounds is described, containing in addition to water a) 10 to 700 g/l of one or more crop protection active compounds,
b) 5 to 150 g/l of one or more dispersants,
c) 50 to 500 g/l of one or more wetting agents,
d) 0.5 to 5 g/l of one or more thickeners and
e) if appropriate an organic solvent and processes for preparation thereof are described.

7 Claims, No Drawings

AQUEOUS, MULTIPHASE, STABLE FINISHED FORMULATION FOR CROP PROTECTION ACTIVE COMPOUNDS AND ITS PREPARATION

This application has been filed under 35 USC 371 from international application PCT/EP94/02085, filed Jun. 27, 1994.

The present invention relates to an aqueous, multiphase, stable finished fomulation for crop protection active compounds, containing in addition to water a) 10 to 700 g/l of one or more crop protection active compounds, b) 5 to 150 g/l of one or more dispersants, c) 50 to 500 g/l of one or more wetting agents, d) 0.5 to 5 g/l of one or more thickeners and e) if appropriate an organic solvent The invention additionally relates to processes for preparing these finished formulations and the use of crop protection active compounds for preparing finished formulations of this type.

To achieve a uniform wetting of the plants to be treated, to improve the absorption of the active compound into the plants to be treated and to assist the transport of the active compounds into the treated plants, additional auxiliaries, e.g. wetting agents, are added to the crop protection active compounds before use. These auxiliaries can either already be added to the formulation of the crop protection active compound or they can be added by the user of the spray liquor of the active compound.

With regard to simple and safe handling and problem-free metering ability of these auxiliaries by the user and with regard to the avoidance of packaging which additionally has to be disposed of, formulations of crop protection active compounds are preferred which already contain auxiliaries of this type.

Since these wetting agents in general are liquid or waxy compounds, they can only be used in particular cases for preparing solid formulations. However, in order to obtain the powdery consistency of solid formulations, the liquid wetting agents have to be absorbed in a separate working step on absorbent materials such as silica gel and ground, which significantly increases the formulation costs and at the same time limits the amount of wetting agent which can be employed. For the user, highly concentrated stable multiphase mixtures are more advantageous, since they are optimized with regard to biological activity and problems in mixing in the spray tank do not apply (D. Seaman, Pesticide Sci., 1990, 29, 439-449; Trends in the Formulation of Pesticides). Liquid finished formulations (formulations of crop protection active compounds and auxiliaries) are therefore customarily sold.

Emulsion concentrates (EC) and suspension concentrates (SC), for example, are known from the literature as liquid formulations for crop protection active compounds (cf. Th. F. Tadros, Disperse Systems in Pesticidal Formulations; Advances in Colloid and Interface Science, 32 (1990) 205-234), an organic solvent in the case of the emulsion concentrates and water in the case of the suspension concentrates being used as a medium or carrier.

A disadvantage of the EC formulation is the use of relatively large amounts of organic, usually readily flammable solvents which result in additional endangering of the user and increased pollution of the environment.

In the preparation of suitable SC formulations, on the other hand, the problem poses itself that because of the frequently poor solubility in water of the wetting agents customarily used, a homogeneous or stable homogeneous formulation cannot be obtained.

It is an object of the present invention to provide a phase-stable finished formulation of crop protection active compounds and auxiliaries which do not have the above disadvantages.

We have now found the finished formulation described at the beginning. Processes for the preparation of finished formulations of this type have additionally been found.

The finished formulations according to the invention in general contain from 10 to 700 g/l, preferably from 50 to 600 g/l, in particular from 100 to 500 g/l, of one or more crop protection active compounds.

In the finished formulations according to the invention, fundamentally all crop protection active compounds can be prepared whose melting point is at least 50° C. The preparation of crop protection active compounds having a lower melting point is in general likewise possible if suitable process conditions are adhered to in the preparation. Examples of suitable crop protection active compounds are, inter alia, 2-chloro-4-ethylamino-6-isopropylamino-1,3,5-triazine (atrazine), methyl 1H-benzimidazol-2-ylcarbamate (carbendazime), 5-amino-4-chloro-2-phenylpyridazin-3 (2H)-one (chloridazone), 3-ethoxycarbonylaminophenyl phenylcarbamate (desmedipham), rel-(2R, 3S)-3-(2-chlorophenyl)-2-(4-fluorophenyl)-2-[(1H-1,2,4-triazol-1-yl) methyl]oxirane (epoxiconazole), N,N-dimethyl-N'-[4-(1-methylethyl)phenyl]urea (isoproturon), 2-chloro-N-(2,6-dimethylphenyl)-N-(1H-pyrazol-1-ylmethyl)acetamide-(metazachlor), 3-(4-bromophenyl)-N-methoxy-N-methylurea (metobromuron), 3-[(methoxycarbonyl)amino] phenyl (3-methylphenyl)carbamate (phenmedipham), dimethyl [1,2-phenylenebis(iminocarbonothioyl] biscarbamate (thiophanate-methyl) and (R,S)-3-(3,5-dichlorophenyl)-5-ethenyl-5-methyl-2,4-oxazolidinedione (vinclozoline), particularly preferably epoxiconazole.

The finished formulations according to the invention additionally contain from 5 to 150 g/l, preferably from 20 to 120 g/l, in particular from 40 to 80 g/l, of one or more dispersants (B).

Suitable dispersants (emulsifiers) (B) can be both compounds of the type which act via the effect of steric hindrance (B1) and anionic dispersants (B2) having electrostatic action.

Commercially available water-soluble dispersants of anionic and nonionic character of the following structural classes can be used:

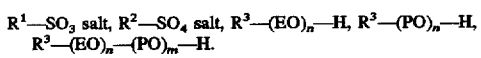

In the above formulae, the substituents and indices used have the following meanings $R^1$—is straight-chain or branched alkyl having 1 to 20 C atoms, preferably having 8 to 18 C atoms, for example dodecyl;

aryl, e.g. phenyl or naphthyl;

aryl, in particualr phenyl which carries a straight-chain or branched alkyl group as mentioned above, e.g. dodecylphenyl;

a condensation product of phenol with urea and formaldehyde;

$R^2$—is straight-chain or branched alkyl having 1 to 20 C atoms, preferably having 8 to 18 C atoms, for example dodecyl;

polyethoxy having 2 to 5 ethoxy units and which carries a straight-chain or branched alkyl group;

polyethoxy having 2 to 25 ethoxy units and which carries an aryl radical substituted by straight-chain or branched alkyl, e.g. nonylphenylpolyethoxy having 20 ethoxy units;

$R^3$—is straight-chain or branched alkyl having 1 to 20 C atoms, preferably having 8 to 18 C atoms, for example dodecyl;

aryl, in particular phenyl, which carries a straight-chain or branched alkyl group as mentioned above, e.g. dodecylphenyl;

n and m independently of one another are an integer of from 4 to 12;

EO is ethylenoxy and

PO is propylenoxy.

Suitable nonionic dispersants are additionally propylene oxide/ethylene oxide block copolymers of the formula

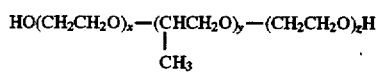

where x, y and z are numbers which are selected such that the molecular weight as a whole is above 1,000. The surfactants of this type used in practice are in general mixtures of several compounds of this formula which differ in the values of x, y and z. As a result, fractions can also be calculated as mean values for these indices. These compounds, as is known, are prepared by addition of ethylene oxide to polypropylene glycol. Examples are PLURONIC® PE 6200 and PLURONIC® PE 10500.

Suitable anionic dispersants (B2) are polymers having a molecular weight of, as a rule, 300 to 1,500 and an anionic group. As a result of the use of polymers of low molecular weight, the viscosity of the finished formulation is reduced compared with formulations which contain polymers of higher molecular weight.

Dispersants which can be used are all surface-active substances customary as auxiliaries for the formulation of crop protection agents. A preferred dispersant is the sodium salt of a condensation product of phenolsulfonic acid, urea and formaldehyde. Such condensation products are described, for example, in DE-A 11 13 457 and DE-A 11 78 081. An example of this class of compound is Wettol® D1 (BASF).

In the block copolymers, a product containing a polyoxypropylene oxide core having a molecular weight of 3,000 to 3,500 and an ethylene oxide content of 50%, i.e. having a total molecular weight of about 6,000 to 7,000, is preferred. Examples of this dispersant are the Pluronic® brands of the BASF-Wyandotte Corporation.

The finished formulations according to the invention can either contain a sterically active dispersant (B1) or an anionic dispersant (B2) or a mixture of B1 and B2. When dispersants of group (B1) and group (B2) are used simultaneously, the weight ratio (B1)/(B2) is customarily from 1:1 to 5:1, preferably from 1:1 to 3:1, in particular from 1:1 to 2:1.

The following products can be used as wetting agents (C) in the multiphase mixture according to the invention:

Polyoxyethylene/polyoxypropylene block copolymers, e.g. as disclosed in U.S. Pat. Nos. 2,677,700, 2,674,619 and EP-A 298 909; particularly suitable products of this group are commercially available, for example, under the name PLURONIC® (BASF Wyandotte Corp.), e.g. PLURONIC® PE 3100, PE 6100 and PE 8100).

Polyoxyethylene or polyoxyethylene/polyoxypropylene fatty alcohols, e.g. as disclosed in GB-A 643 422 or Satkowski et al., Ind. Eng. Chem. 49 (1957) 1875; particularly suitable products of this group are commercially available, for example, under the name WETTOL® LF (BASF).

Polyoxyethylene or polyoxyethylene/polyoxypropylene fatty amines, e.g. as known from Stache, Tensidtaschenbuch [Surfacrant Handbook], Carl Hauser-Verlag Munich, Vienna, 2nd edition, p. 133; particularly suitable products of this group are commercially available, for example, under the name ATPLUS® (Atlas) and Ethomeen® (Akzo).

Fatty acid esters or fatty acid ester ethoxylates, e.g. as disclosed in U.S. Pat. No. 1,914,100; particularly suitable products of this group are commercially available, for example, under the names ARLACEL®, ATMER®, ATMOS® and ATPET® (Atlas).

Polyoxyethylene or polyoxyethylene/polyoxypropylene oxyalcohols, e.g. as disclosed in U.S. Pat. Nos. 2,508,035, 2,508,036, 2,617,830; particularly suitable products of this group are commercially available, for example, under the names LUTENSOL AO® and LUTENSOL TO® (BASF).

Polyoxyethylene or polyoxyethylene/polyoxypropylene alkylphenols, e.g. as disclosed in FR-A 842 943; particularly suitable products of this group are commercially available, for example, under the name LUTENSOL AP® (BASF).

The finished formulations according to the invention contain from 50 to 500 g/l, preferably from 50 to 400 g/l, in particular from 100 to 300 g/l, of a wetting agent (C).

The wetting agents (C) in the finished formulations are used to assist the biological action of the formulation by promoting the wetting and/or the transport of the active compound on the surface and into the plant.

Fundamentally, suitable wetting agents for the finished formulation according to the invention are those whose CMC in water is <1%, preferably from $1\times10^{-5}$% to $1\times10^{-2}$%.

Depending on the nature of the wetting agents used, it may be advantageous to stabilize the finished formulation by the addition of an organic solvent. Whether the addition of a solvent is necessary depends in general on the interfacial tension of the wetting agent used toward water. This addition can thus be dispensed with when using wetting agents having a relatively high interfacial tension. If a wetting agent having a relatively low interfacial tension is used, it is recommended to add at least 10% by weight of an organic solvent, based on the amount of wetting agent. In general, an amount of at most 150% by weight of solvent based on the amount of wetting agent is sufficient. Larger amounts of solvent do not have a disadvantageous effect on the stability of the finished formulation. They only lead to increased and thus undesired pollution of the environment and are additionally uneconomical.

The interfacial tension of the wetting agent used or of the mixture of wetting agent and organic solvent used relative to water at 20° C. is advantageously selected such that it is at least $3\times10^{-1}$ mN/m. In order to exclude mixing effects, the interfacial tension is measured immediately after addition.

When using an additional organic solvent it is additionally to be taken into account that the solubility of the crop protection active compound used is less than 5% in this solvent, since otherwise, on relatively long storage of the finished formulation, crystallization of the active compound and thus destabilization of the formulation can occur as a result of Ostwald crystal growth.

Examples of suitable solvents are aromatic hydrocarbons based on alkylbenzenes such as e.g. xylene, toluene, trimethylbenzene, methylethylbenzene, dimethylethylbenzene, diethylbenzene, tetramethylbenzene and pentamethylbenzene. Mixtures of aromatic hydrocarbons, such as the commercially available solvents with the name Solvesso® (manufacturer Esso) or Shellsol® (manufacturer Shell) are particularly suitable. Solvents on a purely aliphatic basis which can be used are paraffin oil (e.g. Linpar®: $C_{14}$–$C_{17}$ hydrocarbon fraction from Wintershall), but also natural oils such as rapeseed oil and soybean oil if they are able to dissolve the wetting agent sufficiently.

Thickeners used are polysaccharides known from the literature, preferably based on xanthan gum, such as Kelzan® (Kelco, U.S.A.) or Rhodopol® (Rhone-Poulenc).

The thickeners are customarily used in an amount of from 0.5 to 5 g/l; preferably from 1 to 3 g/l.

To prepare a stable finished formulation, a procedure is customarily used in which a suspension concentrate is first prepared in a manner known per se [cf. e.g. EP-A 00 17 001] from one or more solid crop protection active compounds, one or more dispersants and a thickener, and this suspension concentrate is then mixed with a wetting agent and, if desired, an organic solvent.

The suspension concentrate is prepared by grinding the constituents (crop protection active compounds, dispersants and thickeners in a dispersing medium). Water is customarily used here as the dispersing medium.

The solid particles in the suspension concentrate should be present in a grain size range of from 20 to 90%<2 microns, preferably from 40 to 70%<2 microns (measured with a Cilas granulometer 715, Cilas, Marcoussis, France). If the grain size dispersion is too coarse, increased sedimentation occurs, while too fine a dispersion can lead to aggregates of liquid and solid particles which result in flocculation.

The suspension concentrate thus obtained is mixed in a suitable manner with a wetting agent or a mixture of wetting agent and an organic solvent and then diluted with water.

Customarily a procedure is used in which the wetting agent or the mixture of wetting agent and the organic solvent is dispersed in the suspension concentrate in drop form. For dispersion, a minimum energy is required to prevent coalescence to give coarse drops. On the other hand, a maximum energy must not be exceeded. Preferably, the energy density during the mixing is in general from 0.2 to 20 Wh/l, preferably from 1 to 3 Wh/l. Comminution of the drops can be carried out using conventional mixers and dispersers. Annular gap mills of the rotor/stator type are particularly preferably used.

In this process the formation of the stable multiphase mixture according to the invention is expediently carried out in the temperature range of from 10° to 30° C., preferably 15° to 25° C., since too high a temperature endangers the stabilization of the particles by thermal diffusion processes, while too low a temperature prevents the breakdown of the organic liquid phase, as the viscosity decreases.

In addition to said essential constituents, further additives such as antifreezes, bactericides and antifoams can be added to the finished formulations according to the invention.

The emulsification step, i.e. the dispersion in drop form of the wetting agent, or of the wetting agent and solvent admixture in the aqueous medium, is of particular importance for the multiphase mixture according to the invention. According to literature data (cf. H. Schubert et al., Chem. Ing.-Tech. 61 (9), 701 [1989]), the comminution ability is inversely proportional to the interfacial tension and the Weber number (viscosity difference between the disperse and continuous phase) and directly proportional to the Reynolds tension (shear rate difference multiplied by the density of the continuous phase).

Since a particularly low interfacial tension exists in the finished formulation according to the invention as a result of the high wetting agent concentration, the finely divided arrangement should already be able to take place with a low expenditure of energy. Experiments with the finished formulations according to the invention show that for wetting agents of pronounced bipolar structure, which are present in water in micellar structures, different results are obtained although the interfacial tension falls into a no longer measurable low range.

On the basis of these findings it is to be assumed that in the cases described, the micellar constituents are not capable of the formation of a stable separate phase and the formation of the micellar structures must be suppressed or prevented by the addition of a nonpolar additive having a good dissolving power for the wetting agent. As a result, the interfacial tension increases again to higher clearly measurable orders of magnitude. For the stabilization of the newly formed drops, the rapid occupation of the new phase boundary, which is formed after achieving a dynamic equilibrium in accordance with the Gibb's isotherm equation, is additionally important. The restoration of this adsorption equilibrium and the occupation density associated therewith obviously takes place particularly rapidly and completely on the basis of the stability findings using the dispersants described in the examples.

The finished formulations according to the invention are stable in storage, i.e. even on storage over a relatively long period, neither phase separation occurs nor are aggregates formed as a result of phase mixture. The formulations according to the invention furthermore offer the advantage that a biologically optimized and easy-to-use preparation of the crop protection active compound or the crop protection active compounds in combination with the required wetting agents is available to the user. The separate metering in of the auxiliaries by the user is thus unnecessary.

Examples of finished formulations according to the invention are assembled in the following tables i to 11.

TABLE 1

| | Component | Amount [g/l] | Name |
|---|---|---|---|
| A | Active compound | 200 | Chloridazone |
| B1 | Dispersant 1 | 30 | Pluronic ® PE 10500 |
| B2 | Dispersant 2 | 20 | Wettol ® D1 |
| C | Wetting agent | 100 | Wettol ® LF 204 |
| E | Solvent | 100 | Xylene |
| D | Thickener | 2 | Kelzan ® S |

TABLE 2

| | Component | Amount [g/l] | Name |
|---|---|---|---|
| A | Active compound | 100 | Carbendazime |
| B1 | Dispersant 1 | 30 | Pluronic ® PE 10500 |
| B2 | Dispersant 2 | 20 | Wettol ® D1 |
| C | Wetting agent | 200 | Wettol ® LF 700 |
| E | Solvent | 150 | Solvesso ® 200 |
| D | Thickener | 2 | Kelzan ® KQ 14 b |

TABLE 3

| Component | | Amount [g/l] | Name |
|---|---|---|---|
| A | Active compound | 300 | Atrazine |
| B1 | Dispersant 1 | 20 | Pluronic ® PE 10500 |
| B2 | Dispersant 2 | 20 | Wettol ® D1 |
| C | Wetting agent | 100 | Pluronic ® PE 6100 |
| E | Solvent | 100 | Toluene |
| D | Thickener | 1.5 | Rhodopol ® 23 |

TABLE 4

| Component | | Amount [g/l] | Name |
|---|---|---|---|
| A | Active compound | 300 | Vinclozoline |
| B1 | Dispersant 1 | 30 | Pluronic ® PE 10500 |
| B2 | Dispersant 2 | 30 | Wettol ® D1 |
| C | Wetting agent | 100 | Arlacel ® 121 |
| E | Solvent | 80 | Toluene |
| D | Thickener | 1 | Rhodopol ® AX |

TABLE 5

| Component | | Amount [g/l] | Name |
|---|---|---|---|
| A | Active compound | 300 | Vinclozoline |
| B1 | Dispersant 1 | 30 | Pluronic ® PE 10500 |
| B2 | Dispersant 2 | 30 | Wettol ® D1 |
| C | Wetting agent | 100 | Atmer ® 105 |
| D | Thickener | 1.5 | Rhodopol ® 23 |

TABLE 6

| Component | | Amount [g/l] | Name |
|---|---|---|---|
| A | Active compound | 200 | Metobromuron |
| B1 | Dispersant 1 | 30 | Pluronic ® PE 10500 |
| B2 | Dispersant 2 | 40 | Wettol ® D1 |
| C | Wetting agent | 100 | Atmos ® 300 |
| E | Solvent | 50 | Paraffin oil $C_{14}$-$C_{17}$-Linpar ® |
| D | Thickener | 2 | Rhodopol ® MD |

TABLE 7

| Component | | Amount [g/l] | Name |
|---|---|---|---|
| A | Active compound | 150 | Epoxiconazole |
| B1 | Dispersant 1 | 30 | Pluronic ® PE 10500 |
| B2 | Dispersant 2 | 40 | Wettol ® D1 |
| C | Wetting agent | 200 | Wettol ® LF 700 |
| E | Solvent | 150 | Solvesso ® 200 |
| D | Thickener | 1 | Kelzan ® S |

TABLE 8

| Component | | Amount [g/l] | Name |
|---|---|---|---|
| A | Active compound | 150 | Epoxiconazole |
| B1 | Dispersant 1 | 30 | Pluronic ® PE 10500 |
| B2 | Dispersant 2 | 40 | Wettol ® D1 |
| C | Wetting agent | 100 | Lutensol ® A03 |
| E | Solvent | 50 | Solvesso ® 200 |
| D | Thickener | 3 | Kelzan ® |

TABLE 9

| Component | | Amount [g/l] | Name |
|---|---|---|---|
| A | Active compound | 150 | Epoxiconazole |
| B1 | Dispersant 1 | 30 | Pluronic ® PE 10500 |
| B2 | Dispersant 2 | 40 | Wettol ® D1 |
| C | Wetting agent | 100 | Lutensol ® AP 6 |
| E | Solvent | 100 | Xylene |
| D | Thickener | 3 | Rhodopol ® AX |

TABLE 10

| Component | | Amount [g/l] | Name |
|---|---|---|---|
| A | Active compound | 150 | Isoproturon |
| B1 | Dispersant 1 | 20 | Pluronic ® PE 10500 |
| B2 | Dispersant 2 | 30 | Wettol ® D1 |
| C | Wetting agent | 100 | Ethomeen ® T/25 |
| E | Solvent | 150 | Solvesso ® 200 |
| D | Thickener | 3 | Rhodopol ® MD |

TABLE 11

| Component | | Amount [g/l] | Name |
|---|---|---|---|
| A | Active compound | 150 | Epoxiconazole |
| B2 | Dispersant 2 | 50 | Soprophor ® FL |
| C | Wetting agent | 100 | Wettol ® LF 700 |
| F | Solvent | 100 | Trimethylbenzene |
| D | Thickener | 2 | Kelzan ® S |

The mixtures assembled in Tables 1 to 11 are in each case made up to 1,000 ml with water.

Preparation Examples

EXAMPLE 1

400 g of chloridazone, 40 g of PLURONIC PE® 10500, 40 g of WETTOL D1®, 40 g of 1,2-propylene glycol, 3.2 g of KELZAN® S[a], 4.0 g of PROXEL® GXL[b] and 3.0 g of SILICON SRE[c] were made up to 1 l with water and then ground in a ball mill to a particle size of 80%<2 microns (measured by Cilas 715).

500 ml of a solution of 60 parts by weight of WETTOL® LF 700[d] with 40 parts by weight of SOLVESSO® 200[e] were stirred at room temperature into the suspension thus prepared using a propeller stirrer at an energy density of 1 Wh/l.

The formulation thus prepared had a viscosity of 110 mPas at 20° C. and a shear rate of 100 s$^{-1}$. A stable multiphase mixture was obtained in which the particle size was 68%<2 microns.

a xanthan gum thickener, Kelco Co.
b bactericide, ICI
c antifoam, Wackerchemie
d $C_{12}$–$C_{14}$ fatty alcohol alkoxylate, BASF
e $C_{11}$/$C_{12}$ alkylbenzene derivate, EXXON

EXAMPLES 2 to 12

The compositions specified in Tables 1 to 11 are processed according to Example 1 to give a stable multiphase mixture by making up the active compound A together with the dispersant B1 and if appropriate B2, the thickener D and 4.0 g of Proxel® GXL to 1 l with water and then grinding in a ball mill to a particle size of 70%<2 microns (measured by Cilas 715).

The constituent C, if appropriate dissolved, was stirred into the suspension thus prepared using a rotor/stator mill (type K/60/S from Probst and Klaus, Rastatt) with a closed or slightly open gap at an energy density of 2 Wh/l.

We claim:

1. An aqueous, multiphase, stable finished formulation for crop protection active compounds containing, in addition to water,
   a) 10 to 700 g/l of one or more crop protection active compounds,
   b) 10 to 70 g/l of one or more block polymers, as dispersants, which consist of a polyoxypropylene core of molecular weight 3,000 to 3,500 and the remainder to a combined molecular weight of 6,000 to 7,000 comprising ethylene oxide units,
   c) 5 to 80 g/l of an anionic dispersant,
   d) 50 to 500 g/l of one or more wetting agents from the group consisting of polyoxyethylene and polyoxyethylene-polyoxypropylene fatty alcohols,
   e) 0.5 to 5 g/l of one or more thickeners and
   f) if appropriate an organic solvent.

2. A finished formulation as claimed in claim 1, which contains epoxiconazole as the crop protection active compound.

3. A finished formulation as claimed in claim 1 in which the CMC of the wetting agent used is from $1 \times 10^{-5}$ to $1 \times 10^{-2}$% in distilled water.

4. A finished formulation as claimed in claim 1, in which the interfacial tension of the wetting agent used relative to water at 20° C. is at least $3 \times 10^{-1}$ mN/m.

5. A process for preparing a finished formulation as claimed in claim 1, which comprises
   a) preparing a suspension concentrate from 10 to 700 g/l of one or more solid crop protection active compounds, one or more dispersants as set forth in claim 1(b), a dispersant as set forth in claim 1(c) and 0.5 to 5 g/l of one or more thickeners by grinding,
   b) mixing this suspension concentrate with a wetting agent as set forth in claim 1(d) and if appropriate an organic solvent, and
   c) dispersing this mixture in water.

6. A process for preparing a finished formulation as claimed in claim 5, wherein the energy density during the mixing is 0.2 to 20 Wh/l.

7. A method of applying a crop protection active compound to a crop in need thereof, comprising applying said crop protection active compound as the finished formulation of claim 1.

* * * * *